United States Patent
Ihde

(10) Patent No.: US 6,402,516 B2
(45) Date of Patent: Jun. 11, 2002

(54) JAW IMPLANT

(76) Inventor: Stefan Ihde, Lindenstr. 68, CH-8738 Uetliburg (CH)

( * ) Notice: Subject to any disclaimer, the term of this patent is extended or adjusted under 35 U.S.C. 154(b) by 0 days.

(21) Appl. No.: 09/829,351

(22) Filed: Apr. 9, 2001

Related U.S. Application Data

(63) Continuation of application No. 09/437,643, filed on Nov. 10, 1999, now abandoned.

(51) Int. Cl.[7] ................................. A61C 8/00
(52) U.S. Cl. ....................................... 433/176
(58) Field of Search ................. 433/176, 173, 433/174, 172

(56) References Cited

U.S. PATENT DOCUMENTS

| | | | | |
|---|---|---|---|---|
| 4,187,609 A | | 2/1980 | Edelman | 433/176 |
| 4,344,757 A | * | 8/1982 | Streel | 433/173 |
| 4,768,956 A | | 9/1988 | Kurpis | 433/173 |
| 4,815,974 A | * | 3/1989 | Scortecci | 433/173 |
| 4,964,801 A | * | 10/1990 | Kawahara et al. | 433/173 |
| 5,312,255 A | * | 5/1994 | Bauer | 433/174 |
| 5,344,457 A | * | 9/1994 | Pilliar et al. | 623/16 |
| 5,571,017 A | | 11/1996 | Niznick | 433/174 |

FOREIGN PATENT DOCUMENTS

| | | |
|---|---|---|
| DE | 298 12 642 | 7/1998 |
| EP | 0 214 962 | 6/1990 |
| EP | 0 388 576 | 9/1990 |
| FR | 2 302 715 | 10/1976 |
| FR | 75 07078 | 10/1976 |

* cited by examiner

*Primary Examiner*—Nicholas D. Lucchesi
*Assistant Examiner*—Melba Bumgarner
(74) *Attorney, Agent, or Firm*—Husch & Eppenberger, LLC; Robert E. Muir

(57) ABSTRACT

A jaw implant for receiving and mounting of artificial teeth or a prosthetic overstructure has a disk-shaped foot part which may be inserted in an upper or lower jaw, a shaft oriented orthogonally to the foot part, a structure providing an abutment and arranged at one side on the shaft, and a web which connects the shaft with the foot part to form a one-piece jaw implant. The foot part transmits force and is formed as a disk-shaped form body composed of different geometric base forms. The form body is articulated through the web on the shaft.

22 Claims, 3 Drawing Sheets

JAW IMPLANT

CROSS-REFERENCE TO RELATED APPLICATIONS

This application is a continuation of U.S. application Ser. No. 09/437,643 filed Nov. 10, 1999, now abandoned, which claimed priority of German Application No. 298 20 487.8 filed on Nov. 11, 1998, German Application No. 299 08 207.5 filed on May 4, 1999, and European Application No. 99 250 289.8 filed on Aug. 25, 1999.

TECHNICAL FIELD

The present invention relates generally to dental implants and more particularly to a basal osseo integrated jaw implant for receiving and securing a prosthesis such as a crown, a web or a bridge.

BACKGROUND OF THE INVENTION

Basal osseo integrated, lateral jaw implants, may be inserted in an implant bed which is surgically placed in the upper or lower jaws. After sufficient healing, lateral jaw implants serve as a means for securing a crown, artificial teeth or prosthetic tooth constructions. These jaw implants are already generally known in many different embodiment forms. These jaw implants are composed substantially of a ring or disk-shaped foot part which is connected through a web to a shaft that is orthogonal to the foot part. The shaft has at its free end an abutment without a thread, for securing a dental overstructure or an external and internal thread for receiving the abutment.

The known solutions can be subdivided into jaw implants with a single-part design or those with a multi-part design, and are disclosed for example in such patent documents as FR 75 07 078, EP 0 214 962, and DE 298 12 642.

Despite the good results which are obtained with the known jaw implants, it has been shown that with the formation of the implant bed and the insertion of the implant into a surgically produced opening, it is very difficult to perfectly adapt the implant into the anatomy of the upper and lower jaws, without having to subsequently re-position the implant. Also, it is often necessary to subsequently adjust the implant by bending the implant web. Naturally, this can be performed only to a limited extent and with the danger of loosening the jaw implant in the upper or lower jaws. The known basal osseo integrated jaw implants have a shape which is often not suitable for the treatment course.

The patent documents FR 2 302 715, EP 0 388 576 and EP 0 214 962 further disclose the construction of jaw implants in which the upper surface of the foot part of the implant and the transition region of the shaft to the web, the so-called shaft neck, are increased by a jet process, an etching process or combined methods, or the transition region is provided with a profiling or a special structure for supporting the secure seating of the implant shaft in the jaw bone. However, in practice it has been shown that due to the structure and the surface increase in this transition region, irritations and inflammations of the connecting tissue may result during the healing process. In addition, the surface increases can lead to an accumulation of bacteria, which can detrimentally affect the healing process and the permanent, secure seating of the jaw implant in the upper or lower jaws.

SUMMARY OF THE INVENTION

Accordingly, it is an object of the present invention to provide a jaw implant, which avoids the disadvantages of the prior art.

More particularly, it is an object of present invention to provide a jaw implant which, due to a suitable design of the foot part, guarantees wide possibilities for the adaptation of the implant to the varying anatomies in the formation of upper and lower jaws, allows for simple insertion, and provides for complication-free growth of the implant into the jaw bone and secure and permanent fit.

In accordance with the present invention is provided a jaw implant for mounting a dental prosthesis such as artificial teeth, including a force-transmitting foot part for insertion into a jaw; a shaft which is generally orthogonal to the foot part and having a distal end and a base operatively connected to the foot part; and the foot part and a portion of the shaft adjacent thereto having a surface increase for implanting; a portion of the shaft adjacent the distal end having a smooth, non-irritating surface; and the surface increase portion of the shaft being about one-half the total length of the shaft The basal osseo integrated jaw implant in accordance with the present invention preferably has a combined, disk-shaped and ring-shaped foot part comprised of different geometric base forms, on which the shaft for receiving and securing a tooth replacement is connected through a web. The web is arranged preferably eccentrically to the center of gravity of the foot part and connects together the portions of the foot part of the different geometrical forms. The foot part, the web and the transition region of the shaft to the web is provided with a surface increase produced in a known manner with a jet, etching or combined processes, while the shaft in its head region has a smooth, non structured surface below the thread or the abutment.

Substantial conformity of the foot part of the jaw implant to the opening produced by the milling in the upper or lower jaw is guaranteed due to the fact that the load-supporting foot part is formed of circular/elliptical and rectangular/square geometrical form portions and the web is arranged eccentrically to the foot part center of gravity and receives the shaft of the implant. Simultaneously, the configuration of the foot part thus formed prevents the inserted implant from turning in the surgically produced implant bed.

The ring-shaped edge, which is produced by recesses provided in the foot part on both sides of the web, together with the inventive configuration secures an exact placement of the foot part in the compacta of the upper and/or lower jaws and thereby provides conditions for a long term, fixed seating of the jaw implant.

In accordance with another embodiment of the present invention, the force-transmitting foot part is composed of two disk rings which merge into one another and are formed by circular or elliptic form bodies. The shaft, which is provided on the end side with a thread for securing an abutment, is arranged eccentrically to the foot part center of gravity through a web in the center of a disk ring. A web which is positioned at one side to the inside wall of the disk ring can be used as well, instead of a continuous web. As already mentioned, the foot part, the web and the transition region of the shaft to the web are provided with a known surface increase, while the shaft in its head region has a smooth, non structured surface.

With this type of implant, the occurring forces can be further transmitted from the shaft, for the reception and securing of the dental prosthetic overstructure in the upper or lower jaws. With the surgical introduction of the implant, the shaft can be seated on the prosthetically desired place, and a range of bone that is more remote from the shaft can be used for force transmission. It is especially advantageous to use this implant design in the region of the first and second upper molars, since generally there are still sufficient tuber bones available at a distance from this jaw region, in spite of the fact that there are no teeth required here. However, also in the lower jaw side tooth region the basal osseo integrated jaw implants with asymmetrical shaft arrangement are advantageous. The chewing force transmitting implant surfaces can thus be distributed over the jaw, while the shafts of the implants can be integrated in a favorable medial position against the centrifugal resorption of the lower jaw. When compared with the implants with flat longitudinal sides or implant sides, the implant forms with the foot part formed of two disk rings which merge into one another, has the advantage of a simpler introduction. For producing the implant bed, a round slot with cortical anchoring can be milled by merely using the same size milling tool. The milling extends in an advantageous manner from a single point and then, depending on the desired disk size, advances in the different directions with respect to the center points of the disk rings, which can even be angled relative to one another in a horizontal direction. In the implant bed produced by the corticalic penetration, the implant is first inserted with the shaft-free disk ring and then turned into the correct position.

Due to the eccentric arrangement of the web and shaft relative to the foot part center of gravity and the proposed configuration of the foot part, the conditions are provided for an easy and substantial adaptation of the implant to the different natural anatomy of the upper and lower jaws in the process of the surgical operation and, depending on the formation of the jaw bone crest, in most applications work can only be carried out in one milling direction. Counter milling for forming the implant bed as was often necessary with the use of implants having a central arrangement of the shaft and the foot part, but an asymmetrical base form (FR 7507078), can be dispensed with. The formation of the basal osseo integrated jaw implant in accordance with the present invention leads simultaneously to an improved shortening of the milling time for the implant bed and thereby of the length of the operations.

Subsequent adaptations and corrections after the ingrowth of the implant into the upper and lower jaws, for example by bending of the shaft, which naturally result in a danger of loosening of the implant in the jaw bone, can be avoided.

While the surface enlargement of the foot part, the web and in some cases the transition region and recesses provided in the foot part enhances a fast ingrowth of the implant and its secured seating in the upper and lower jaws, the shaft, which is free from the surface increase and structuring, prevents the formation of plaque in the thread-adjacent head region, while a microgap can be formed which is rinsed by natural salivation and promotes the formation of infection-free connecting tissue. Infections and inflammations of the connecting tissue are prevented in this region by the microgap and thereby the strong and reliable seating of the implant in the upper or lower jaws is also enhanced. It has been shown that with flexible implant systems, for example with constructions in the lower jaw or during work in upper jaws, infections, which later could lead to bone decay, occurred occasionally in only a few implants on the structured shaft.

Due to the microgap which is formed in the transition region, the shaft and the web of the jaw implant, which is firmly fixed in the compacta of the jaw bone, further have the ability under stress to act resiliently in the spongiosa of the jaw bone. Displacements occur in the regions of the jaw bone, which adjoin the web and the shaft. The likelihood of a long term fixed seating of the jaw implant is thereby also enhanced, while the force transmission is performed always in the compacta.

Advantageously, the height of the surface increases to the free smooth part of the shaft, amounts to at least half of the height of the shaft to the thread for securing an abutment or the like. The ratio between the height of the foot body and the height of the shaft is in the range of 1:6–1:30. Thus, it is possible, to provide a good osseo integration of the basal shaft portion far from the region of bacterial contamination.

In another preferred embodiment, the force-transmitting foot part of a one-piece jaw implant has a ring body with a web articulated laterally to the inside wall of the ring body and merging into a shaft which is orthogonal to the foot part and has a bendable neck. Connected to the bendable neck is an abutment integrated as one piece in the shaft for receiving the prosthetic overstructure, and the foot part can have a round or elliptical configuration. This jaw implant variant can be produced in a cost effective manner and has the advantage that after it is implanted in the mouth of the patient, the components of the implant need no further assembly nor to be screwed together.

When compared to the implants known in the art, the proposed jaw implant has substantial advantages in the sense of the required operational features for introduction in the upper and/lower jaw bones and with respect to the necessary adaptation work required during insertion of the overstructure.

Because the web is articulated with one side to the inside wall of the foot part and merges orthogonally into the shaft of the implant, it is unlikely that the connecting tissue will grow from the insertion side over the web of the foot part and into the region of the shaft. The progressive growth of the connecting tissue in the direction toward the shaft takes place namely over the webs. Surprisingly however it has been found that a reduction of the webs also leads to a decrease in the probability of loss for the implant, without increasing the frequency of breakage.

With a suitable choice of materials for the implant and a corresponding structural design of the neck part of the shaft, there is the possibility of bending the abutment in the mouth of the patient in the required direction and thereby to create the conditions for a parallel insertion of multi-bracing bridges.

Advantageously the abutment is measured in such a way that a cementing of the crown or the overstructure can be carried out, and with the embodiment of the implant as a simple cementing post it has an internal thread on the head side. Thereby it is possible to secure also screwable bridges on the implant. It is known that there is a problem that the bridges which are mounted exclusively by cementing are difficult to remove when this is required. However, the inventive solution makes it possible to secure a bridge simultaneously by cementing and screwing. Even if the screws become loose, the bridge is still held in its mounting to a limited extent and vice versa.

In accordance with a further embodiment of the present invention, the force-transmitting foot part is formed by several disk-shaped ring bodies which are spaced from one another, and which are joined via inwardly located webs and connected with one another by an additional shaft oriented orthogonally to the foot part. With this embodiment, an increase in the force-transmitting surfaces is provided in an advantageous manner. As is generally known, the forces are transmitted only in the region of the compact bone, i.e. in the region of the ring body of the foot part, which for this purpose is located completely inside the compactor of the bone.

The ring bodies which are located over one another and are spaced apart from one another can also have varying external diameters. At least one of the ring bodies, preferably the lower ring body, has a continuous web, which is positioned at an angle alpha of 30°–90°, preferably 90°, relative to another web affixed at one side to the inside wall of the other ring body. The foot parts thus formed allow for a substantial adaptation of the implant to the anatomical features of the upper and/or lower jaw and permit the full use of the bone width of the upper and/or lower jaw. The continuous web of the lower ring body is thus located completely in the spongiosa, soft bone region, while the upper web located at right angles to the continuous lower web is completely received by the compacta of the bone, which is not damaged by the milling.

The lower ring body can have a body form which deviates from the upper ring body and is cornered or combined, and has a smaller external diameter than that of the upper ring body. The implants with the foot parts thus designed are recommended in particular in the region of the arteria palatina where the crestal portion of the jaw crest is wider than the basal portion. A rupturing of the artery during the surgical operation for producing the opening for receiving the implant can thereby be avoided.

With a distance between the ring bodies of the foot part exceeding three millimeters, not only the placement of the implant is made easier and its hold in the upper and/lower jaw is improved, but also an improved blood supply of the inter discal region is provided, since the lateral flow from the direction of the mucus membrane is increased. Moreover, the lateral stability of the implant increases. Furthermore, the basal ring body is better protected in the event of bacteria settling on the crestal ring body.

Total implant losses are eliminated. Moreover, the removal of the implant or a disk of the implant is made easier. The insertion of the implant can also be performed more reliably. In particular, for brittle, cortical bones there is less danger of tearing the osteotomised interdiscal region when the ring bodies are positioned further from one another.

In accordance with another embodiment of the present invention, the configuration of the force-transmitting foot part deviates from a square base shape, with at least one side of the base form having a ring-shaped semicircle, while the corners of the opposite side are rounded by radii. The web connecting the shaft with the foot part inaccordance with a particular embodiment is formed of one side and is attached to the inside wall of the semicircular shaped foot part portion. In a further embodiment of this implant type, the web is constructed of two sides and arranged on a vertical or horizontal implant axis. However, the implant shaft can also be connected to the force-transmitting foot part through a cross-shaped web or through several webs formed of one side and offset relative to one another at an angle of 120°.

Particularly with the combined body forms and the configuration which deviates from a square base form, the foot part corresponds almost identically to the form of the implant bed produced by milling and completely fills it.

Altogether the present invention achieves the preconditions for a substantial adaptation of the implant to the anatomy of the upper and lower jaws, for a relatively simple surgical procedure, for a fast and largely complication-free healing of the implant and for a permanent, reliable and secure seating of the implant in the upper or lower jaws.

BRIEF DESCRIPTION OF THE DRAWINGS

Reference is now made to the drawings which illustrate the best known mode of carrying out the invention and wherein the same reference numerals indicate the same or similar parts throughout the several views.

DETAILED DESCRIPTION

Figure 1:
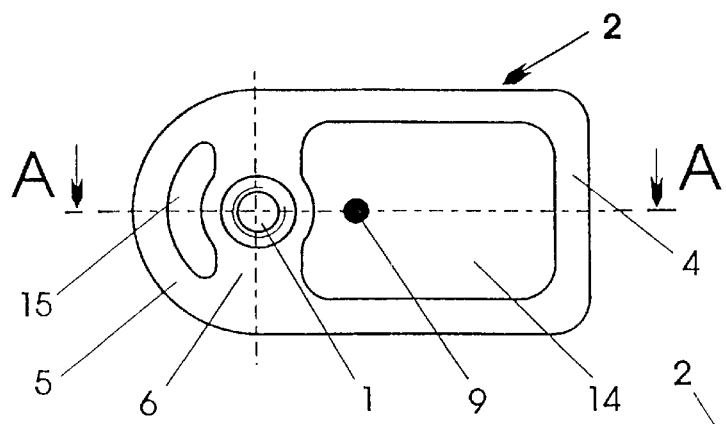
FIG. 1 is a plan view of an implant in accordance with a first embodiment of the present invention.
Figure 2:
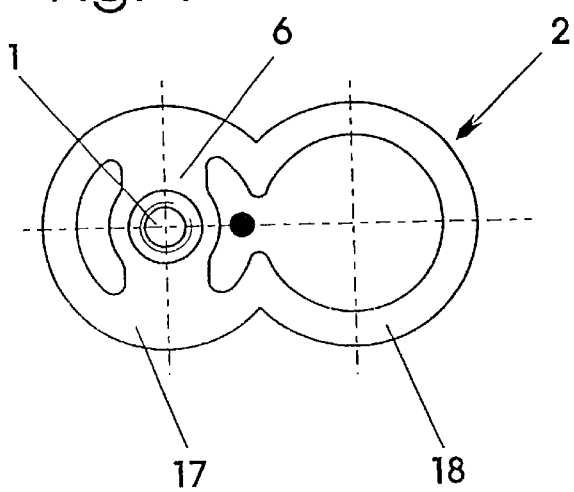
FIG. 2 is a view showing the implant of the present invention with a foot part formed of disk rings.
Figure 3:
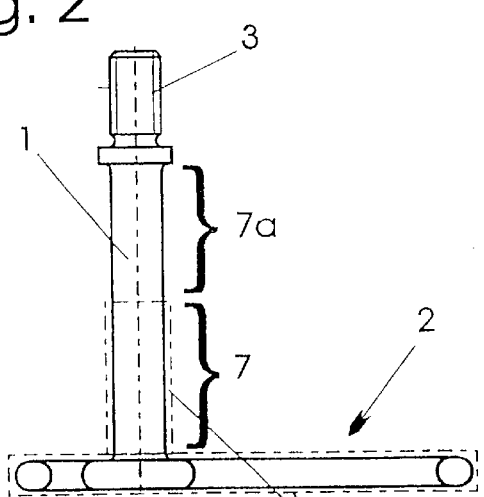
FIG. 3 is a view showing a section taken along the line A—A in FIG. 1.

As can be seen from FIGS. 1 to 3, an implant in accordance with the present invention which is inserted into a surgically constructed implant bed in an upper or lower jaw has a foot part 2 and a shaft 1, which is attached to the foot part 2 through a web 6. The shaft 1 is oriented orthogonally to the foot part 2 and has at its exposed end face a thread 3 which may serve as a means to receive an abutment, or by itself as a cementing post.

In accordance with an embodiment of the present invention, the force-transmitting foot part 2 of the jaw implant has a combined body form of different geometric base forms. In the embodiment shown, it is composed of a circular-elliptical form portion 5 and a rectangular/square form portion 4 with rounded corners.

A continuous web 6, which carries the shaft 1 of the implant, is arranged in the transition region between the geometric form portions 4; 5 in such a way that the shaft 1 and the web 6 are positioned asymmetrically, i.e. outside the plane of the foot part center of gravity 9.

The inventive configuration of the foot part 2 and the non-axial eccentric position of the shaft 1 relative to the foot part center of gravity 9 allow for a substantial adaptation of the jaw implant to the non-uniform, natural anatomy of the upper and lower jaws and to the implant bed which is produced surgically by means of a milling tool.

Figure 12:
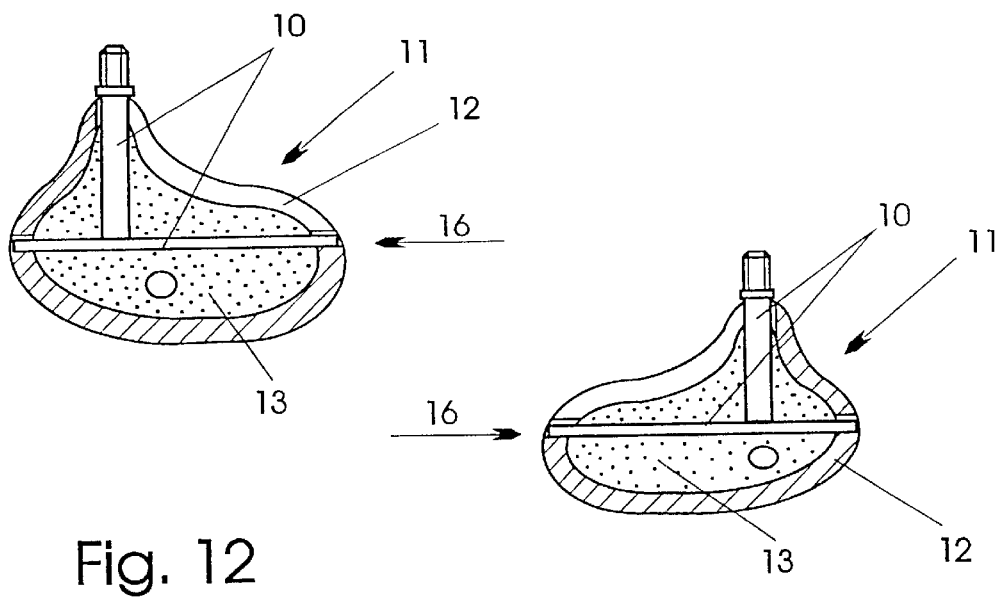
FIG. 12 is a view schematically showing an implant in correspondence with FIG. 1 which is inserted in a lower jaw.

The foot part 2 of the jaw implant further has two recesses 14; 15 which are arranged so that, with the exception of the edge region of the web 6, they produce a ring-shaped design of the foot part 2. After insertion of the jaw implant into the implant bed, the ring-shaped foot part 2, as can be seen from FIG. 12, is positioned substantially in the compacta 12 of the upper and/or lower jaw and secures in this manner a firm seating of the jaw implant 10 in the jaw bone 11. The healing process of the inserted jaw implant and the blood supply in the bone portion adjacent to the jaw crest is further enhanced and aided by the recess 14 and 15.

A further advantageous embodiment of the present invention is shown in FIG. 2. The foot part 2 of the implant 10 is composed of two disk rings 17 and 18 which merge into one another. They may have the same or different diameters or can be formed as circular or elliptical form bodies. The shaft 1 is arranged asymmetrically to the foot part center of gravity 9, in the center of one of the two disk rings 17 and 18, and through a web 6. The shaft 1 at one end carries a thread 3 in a known manner for securing an abutment or for direct securing of a prosthetic construction. Instead of the continuous web 6 shown in FIG. 2, the shaft 1 can also be secured through a one-sided web that is connected or attached to the inside wall of one of the disk rings 17; 18.

Figure 13:
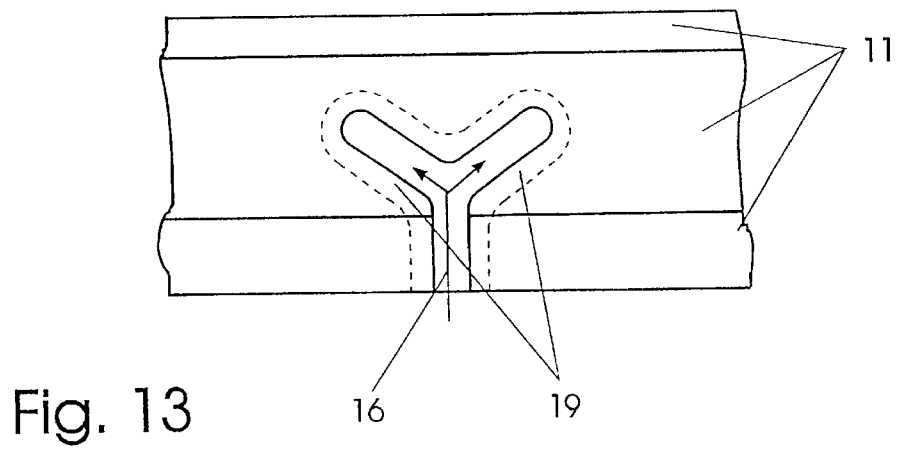
FIG. 13 is a plan view on a portion of the lower jaw with the implant bed for receiving an implant in correspondence with FIG. 2 in a schematic illustration.
Figure 14:
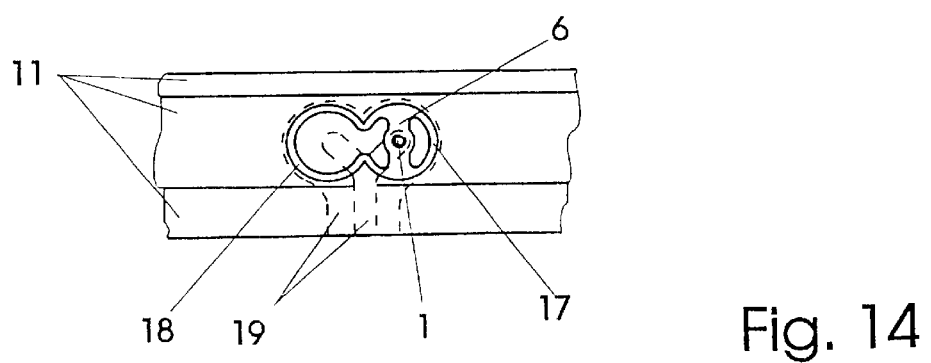
FIG. 14 is a view showing the implant of FIG. 2 inserted in the implant bed of FIG. 13.

For receiving the implant of FIG. 2, an implant bed 19 as shown in FIG. 13 is milled in the upper or lower jaw by corticalic penetration. The implant with the shaft-free disk ring 18 is first inserted into the implant bed 19 thus formed and then turned to a predetermined position as shown in FIG. 14.

Figure 4:
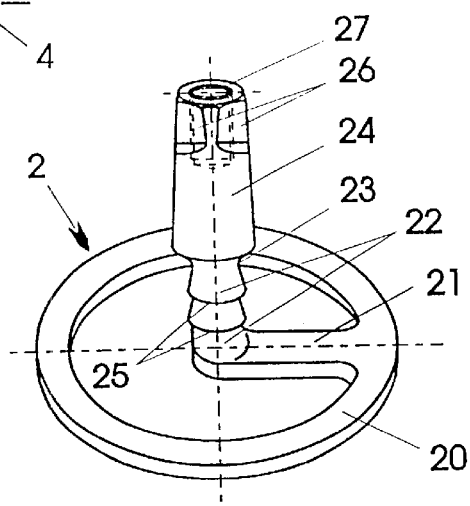
FIG. 4 is a view showing a further embodiment of the inventive jaw implant; which is formed of one piece and provided at its free shaft end with an abutment.

Unlike the known jaw implant, in which the shaft 1 has a profiling or a surface increase, the jaw implant shown in the drawings can be provided in the thread-adjacent head region 7a with a structure-free, smooth surface, while the transition region 7 of the shaft 1 to the web 6 can be provided selectively with a surface enlargement 8 or with a contour 25 corresponding to the implant design of FIG. 4. Due to the smooth surface property of the head region 7a, the deposit of plaque is less likely to occur and the tissue irritations and inflammations which are often caused by profiled and surface-enlarged shaft portions are avoided.

Simultaneously, the shaft 1 and the web 6 under the action of great stress can be minimally resilient in the spongiosa 13 of the jaw bone 11, thereby causing in the transition region 7 an elastic bone deformation to take place. Because of the smooth shaft design when there is minimal resilience of the jaw implant in the spongiosa of the jaw bone, connecting tissue irritations and inflammations are excluded and a long term reliable and complication-free fixed seating of the foot part 2 in the compacta of the upper or lower jaw is guaranteed.

Further advantageous implants with different, variable embodiments of the force-transmitting foot part are shown in FIGS. 4–11.

As can be seen from FIG. 4, the inventive one-piece jaw implant has a force-transmitting foot part 2 in the form of a ring body 20 and with a one-sided web 21, which is attached to the inside wall of the ring body 20 and merges into a shaft 22. During insertion of the implant, this web 22 is introduced by the operator into the bone which is most stable against resorption or, in other words, preferably in the region of the upper jaw at the palatum or in the region of the lower jaw.

The shaft 22 which is oriented orthogonally to the foot part 2 has a bendable neck 23, on which an abutment for receiving the prosthetic overstructure is connected. The abutment 24 has at its free end side receiving surfaces 26 and an internal thread 27, which allows the implant to be screw-connected to the prosthetic overstructure.

A contour 25 is provided in the region of the shaft 22 between the neck 23 and the web 21, whose largest diameter is substantially smaller than the diameter of the ring body 20 of the foot part 2. This contour 25, as described above, improves the adherence of the inserted implant in the upper or lower jaw, so that the deeper growth of the connecting tissue is prevented and a firm growth of the bone is enhanced.

The abutment 24 having the internal thread 27 provides for the ability to screw-connect the prosthetic overstructure to the implant inserted in the upper and lower jaw and to apply to its external surface, which is beveled in a known manner, a retentive cementing and/or adjoining sealing between the receiving surface for the implant in the overstructure and the external surface of the abutment 24.

Figure 5:
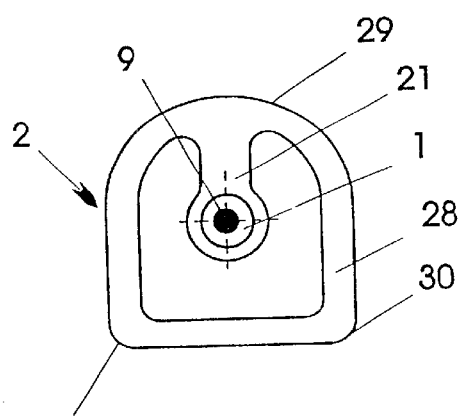
FIG. 5 is a plan view of a jaw implant with ring-shaped foot part, whose configuration deviates from a square base form.
Figure 6:
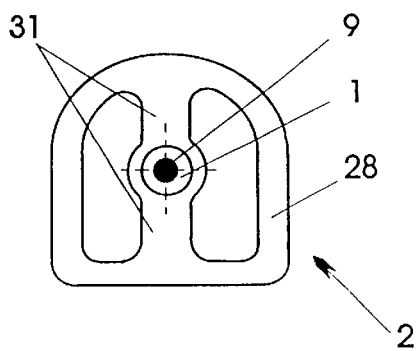
FIGS. 6–9 are views showing the inventive jaw implant of FIG. 5 with different arrangement variants for the web, through which the foot part is connected with the shaft.
Figure 7:
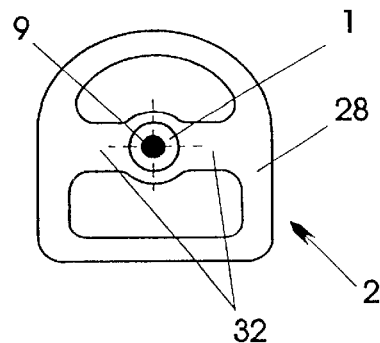
Figure 8:
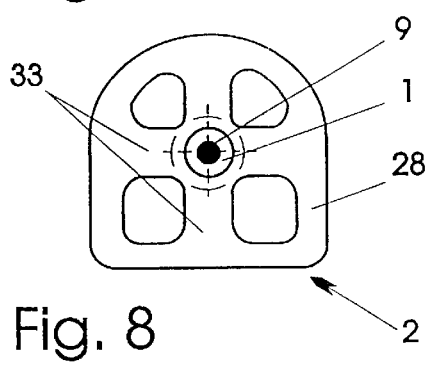
Figure 9:
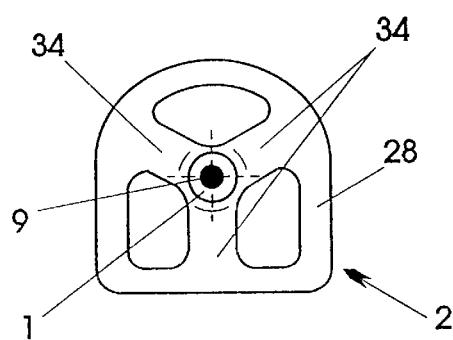

In support of the different embodiments of the implant-foot parts shown in FIGS. 5–11, the ring body 20 can have any cylindrical, elliptical, cornered or combined body form. The edges of the cornered body form portion, as shown in FIG. 5, can be rounded by radii 30. Because of the different body forms, it is possible to provide, in a relatively simple manner, a substantial adaptation of the foot parts to the particular milling tool used or to the implant bed formed in the upper or lower jaw for receiving the implant.

The differently formed and arranged webs 6, 21, 31, 32, 33, 34, 36, 37, through which the shaft 1 is connected to the foot part 2, disappear completely in the depth of the jaw bone and are not subjected to the growth of the faster growing mucus membrane.

Figure 10:
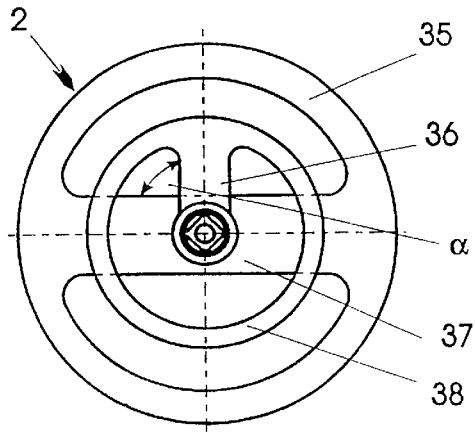
FIG. 10 is a view showing the draw implant of FIG. 4 with a foot part formed of two spaced ring bodies
Figure 11:
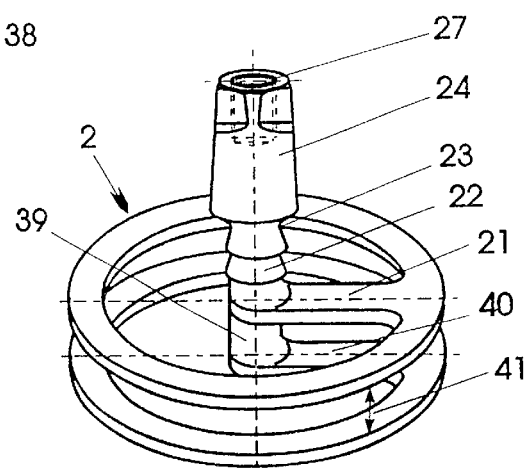
FIG. 11 is a plan view on a jaw implant of FIG. 4, in accordance with another embodiment of the force-transmitting foot part

The embodiments of the jaw implant shown in FIGS. 10 and 11 have substantially the same construction as the implant of FIG. 4. They are, however, different from FIG. 4 in that for improving the seating of the jaw bone they are provided with two ring bodies which are spaced apart from one another and form the foot part 2 of the implant. In accordance with FIG. 11, the ring bodies of the foot part 2, which are spaced apart from one another by a distance 41 greater than 3 mm, have one-sided webs 21 and 40 attached to the inside wall of the ring bodies and connected to one another through an additional shaft 39. As already described above, because of this a greater spacing, which exceeds 3 mm, between the ring bodies of the foot part 2, the setting of the implant is improved, the hold in the upper and/or lower jaw is improved, and improved blood circulation of the interdiscal region is achieved. Moreover, the lateral stability of the implant is increased, while the basal ring body is better protected when the crestal ring body is subjected to bacterial attack.

In the implant variant shown in FIG. 10 the ring bodies 35 and 38 of the foot part 2, which are spaced apart from one another, have different external diameters. An elliptic, cornered or combined configuration which deviates from the cylindrical body 4 can also be provided at least for the ring body 35 which is positioned at a distance from the opposite free end of the shaft 1. The lower ring body 35 of the foot part 2 has preferably a two-sided web 37 which increases the stability of the implant, while the upper ring body 38 has a one-sided web 36, in order to benefit from the advantages provided by the one-sided web formation with regard to the undesired growth of the connecting tissue in the region of the compacta. Both webs are offset relative to one another preferably at an angle of α. After the complication-free ingrowth in the upper and/or lower jaw, with the preferred embodiment according to FIG. 10, an exceptionally stable and highly stress resistant implant construction is produced.

FIGS. 5–9 show different foot parts 2 which deviate from a square base form for a basal osseo integratable implant with different arrangement and design of the webs 21, 31; 32, 33; and 34 which connect the shaft 1 to the foot part 2, wherein at least one body side of the base form is formed ring-shaped by a rounding 29, and the corners of the opposite side are rounded by a radii 30. The shapes of the ring part 28 shown in FIGS. 5–9 guarantee a substantial adaptation to the implant bed produced by milling and to the natural anatomy of the jaw bone with symmetrical positioning of the shaft 1 to the foot part center of gravity 9. As can be seen from FIGS. 5–9, the webs 21; 31; 32; 33 and 34, depending on the configuration of the ring body 28, are formed one-sided in FIGS. 5 and 9 and two-sided in FIGS. 6 and 7 and are arranged along vertical or horizontal implant axes in FIGS. 6 and 7. According to FIG. 8, the two-sided webs 33 have a cross-shape, while in FIG. 9 the one-sided webs 34 are offset from one another at an angle of 120°. Because of the different designs and arrangements of the webs 21; 31; 32; 33; and 34 a further adaptation of the implant to the receiving and to the transmitting forces may be produced.

Other objects, features and advantages will be apparent to those skilled in the art. While preferred embodiments of the present invention have been illustrated and described, this has been by way of illustration and the invention should not be limited except as required by the scope of the appended claims.

I claim:

1. A basal osseo integrated jaw implant for mounting a dental prosthesis such as artificial teeth, including
   an asymmetrical force-transmitting foot part for insertion into a jaw from the lateral side of the jaw;
   a shaft which is generally orthogonal to the foot part and having a distal end and a base operatively connected to the foot part;
   mounting means at the distal end of the shaft for mounting the dental prosthesis; and
   the foot part having a circumferential portion having a surface area which is unequal in size and shape on opposite sides of the shaft and including a generally semicircular side and a flat side remote from the semicircular side, the flat side having opposite ends, the shaft being positioned at the center of an imaginary circle defined by the semicircular side, the shaft being positioned so that the ends of the flat side are further from the shaft than is the semicircular side and the shaft is offset from the center of gravity of the foot part.

2. A basal osseo integrated jaw implant according to claim 1, wherein the circumferential portion of said foot part has one end which is generally rectangular opposite to and connected with the semicircular side, and the flat side defines part of the rectangular shape.

3. A basal osseo integrated jaw implant according to claim 1, including a web which interconnects said shaft and said foot part, and wherein the circumferential portion of the foot part lies within a generally square base form, wherein the opposite ends of the flat side are rounded, and the web is formed by openings in the foot part.

4. A jaw implant according to claim 1, wherein the foot part and a portion of the shaft adjacent thereto have a surface increase for implanting; a portion of the shaft adjacent the distal end having a smooth, non-irritating surface; and the surface increase portion of the shaft being about one-half the total length of the shaft.

5. A jaw implant for mounting a dental prosthesis such as artificial teeth, including
   a force-transmitting foot part for insertion into a jaw, the foot part having two disk rings which merge into one another;
   a shaft which is generally orthogonal to the foot part and having a distal end and a base operatively connected to the foot part, the shaft being connected to the rings through a web asymmetrically to the center of gravity of the foot part and at the center of one of the disk rings; and
   the foot part and a portion of the shaft adjacent thereto having a surface increase for implanting; a portion of the shaft adjacent the distal end having a smooth, non-irritating surface; and the surface increase portion of the shaft being about one-half the total length of the shaft.

6. A basal ossco integrated jaw implant for mounting a dental prosthesis such as artificial teeth, including
   a force-transmitting foot part for insertion into a jaw;
   a shaft which is generally orthogonal to the foot part and having a distal end and a base operatively connected to the foot part;
   the foot part and a portion of the shaft adjacent thereto having a surface increase for implanting; a portion of the shaft adjacent the distal end having a smooth, non-irritating surface the surface increase portion of the saft being about one-half the total length of the shaft;
   mounting means at the distal end of the shaft for mounting the dental prosthesis; and
   wherein the foot part includes two superposed form bodies with different external diameters which are spaced apart on the shaft and connected thereto by separate webs.

7. A jaw implant according to claim 6, wherein the form body positioned furthest away from the distal end of the shaft, has a larger external diameter than the other form body.

8. A jaw implant according to claim 6, wherein the space between the spaced apart form bodies is greater than 3 mm.

9. A basal osseo integrated jaw implant according to claim 6, wherein the shaft and one of the form bodies are connected to each other through a single web, which is firmly attached to an inside wall of the one form body, whereby the shaft is connected to the one form body in a cantilever manner.

10. A jaw implant according to claim 6, wherein the surface increase is formed through jet processes.

11. A jaw implant according to claim 6, wherein the surface increase is formed through etching processes.

12. A jaw implant according to claim 6, wherein the webs of the respective form bodies are positioned with respect to each other at an angle of 30° to 90°.

13. A basal osseo integrated jaw implant for mounting a dental prosthesis such as artificial teeth, including:
   an asymmetrical force-transmitting foot part for insertion into a jaw from the lateral side of the jaw;
   a shaft which is orthogonal to the foot part and having a distal end and a base operatively connected to the foot part;
   mounting means at the distal end of the shaft for mounting the dental prosthesis; and
   the foot part having a circumferential portion having a surface area which is unequal in size and shape on opposite sides of the shaft and including a generally semicircular side and a side remote from the semicircular side, the shaft being positioned at the center of an imaginary circle defined by the semicircular side, the shaft being positioned so that a portion of the remote side is further from the shaft than is the semicircular side and the shaft is offset from the center of gravity of the foot part.

14. A basal osseo integrated jaw implant according to claim 13, including a web which interconnects said shaft and said foot part, and wherein the shaft and the web are positioned in a region outside the center of gravity of the foot part.

15. A basal osseo integrated jaw implant according to claim 13, wherein the foot part includes a web which extends to and merges into the shaft, and the shaft has a bendable neck.

16. A basal osseo integrated jaw implant according to claim 13, wherein the mounting means is constructed and arranged so that a dental prosthesis may be secured by a retentive cement.

17. A basal osseo integrated jaw implant according to claim 13, wherein the mounting means is constructed and arranged so that a dental prosthesis may be secured by an adjoining seal.

18. A basal osseo integrated jaw implant according to claim 13, wherein the foot part further includes a disk-like form bodies which is inter-connected.

19. A basal osseo integrated jaw implant according to claim 13, wherein the shaft is connected to the foot part through webs which are arranged generally in the shape of a cross.

20. A basal osseo integrated jaw implant according to claim 13, wherein the shaft and the foot part are connected through webs, which are arranged at angles of 120° relative to one another.

21. A basal osseo integrated jaw implant according to claim 13, wherein the mounting means includes a screw thread and cement.

22. A basal osseo integrated jaw implant according to claim 13, wherein the implant is manufactured from titanium.

* * * * *